US012728020B2

(12) United States Patent
Finke

(10) Patent No.: US 12,728,020 B2
(45) **Date of Patent: *Sep. 8, 2026**

(54) METHOD FOR PRODUCING A PROSTHETIC LINER AND SYSTEM CONSISTING OF PROSTHETIC LINER AND PROSTHETIC SOCKET

(71) Applicant: OTTOBOCK SE & CO. KGAA, Duderstadt (DE)

(72) Inventor: Lars Benjamin Finke, Landolfshausen (DE)

(73) Assignee: OTTOBOCK SE & CO KGAA, Duderstadt (DE)

( * ) Notice: Subject to any disclaimer, the term of this patent is extended or adjusted under 35 U.S.C. 154(b) by 674 days.

This patent is subject to a terminal disclaimer.

(21) Appl. No.: 17/614,317

(22) PCT Filed: May 20, 2020

(86) PCT No.: PCT/EP2020/064059

§ 371 (c)(1),
(2) Date: Nov. 24, 2021

(87) PCT Pub. No.: WO2020/239571

PCT Pub. Date: Dec. 3, 2020

(65) Prior Publication Data

US 2022/0226129 A1 Jul. 21, 2022

(30) Foreign Application Priority Data

May 29, 2019 (DE) ......................... 102019114461.2

(51) Int. Cl.

| | |
|---|---|
| ***A61F 2/78*** | (2006.01) |
| ***A61F 2/50*** | (2006.01) |
| ***A61F 2/76*** | (2006.01) |
| ***A61F 2/80*** | (2006.01) |
| ***B29C 64/386*** | (2017.01) |
| ***B33Y 50/00*** | (2015.01) |
| ***B33Y 80/00*** | (2015.01) |

(Continued)

(52) U.S. Cl.

CPC .......... *A61F 2/5046* (2013.01); *A61F 2/7812* (2013.01); *A61F 2/80* (2013.01);

(Continued)

(58) Field of Classification Search

None

See application file for complete search history.

(56) References Cited

U.S. PATENT DOCUMENTS 5,314,497 A * 5/1994 Fay ....................... A61F 2/7843 623/33
8,372,159 B2 2/2013 Mackenzie (Continued)

FOREIGN PATENT DOCUMENTS

DE 1849778 U * 4/1962 ............... A61F 2/80
DE 10142491 10/2004

(Continued)

OTHER PUBLICATIONS

International Search Report and Written Opinion issued in PCT/EP2020/064059, mailed Aug. 19, 2020, 7 pgs.

*Primary Examiner* — David H Willse

(74) *Attorney, Agent, or Firm* — HOLLAND & HART LLP

(57) ABSTRACT

The invention relates to a method for producing a prosthetic liner for insertion into a prosthetic socket, which comprises a receptacle having a distal end and a proximal edge for a residual limb and the prosthetic liner. The method comprises determining a sealing lip contour on the outer face of the prosthetic liner which corresponds to a height contour of the proximal edge of the prosthetic socket, or on the basis of available, known anatomic characteristics of the residual limb and arranging a sealing lip on the outer face of the prosthetic liner along the determined sealing lip contour.

19 Claims, 3 Drawing Sheets

(51) Int. Cl.
*A61F 2/60* (2006.01)
*B29L 31/00* (2006.01)

(52) U.S. Cl.
CPC ............ *B29C 64/386* (2017.08); *B33Y 50/00* (2014.12); *B33Y 80/00* (2014.12); *A61F 2002/5049* (2013.01); *A61F 2002/505* (2013.01); *A61F 2002/607* (2013.01); *A61F 2002/762* (2013.01); *A61F 2002/7818* (2013.01); *A61F 2002/802* (2013.01); *B29L 2031/7532* (2013.01)

(56) References Cited

U.S. PATENT DOCUMENTS 10,376,392 B2 8/2019 Schober
12,144,749 B2 * 11/2024 Bause .................. A61F 2/7812
2004/0243252 A1 12/2004 Carstens
2015/0142131 A1 5/2015 Egilsson
2017/0304085 A1 * 10/2017 Kurth .................... A61F 2/7812
2020/0060846 A1 2/2020 Mueller
2020/0356073 A1 * 11/2020 Tokushima ............. G06F 30/10

FOREIGN PATENT DOCUMENTS

| | | |
|---|---|---|
| DE | 202007019684 | 8/2015 |
| DE | 102016114681 | 2/2018 |
| DE | 102017108913 | 10/2018 |
| EP | 2815728 | 6/2016 |
| EP | 3238667 | 1/2017 |
| EP | 3298991 | 3/2018 |
| WO | 2008030346 | 3/2008 |
| WO | 2017189398 | 2/2017 |
| WO | 2018015736 | 1/2018 |
| WO | 2018029188 | 5/2018 |

* cited by examiner

METHOD FOR PRODUCING A PROSTHETIC LINER AND SYSTEM CONSISTING OF PROSTHETIC LINER AND PROSTHETIC SOCKET

CROSS-REFERENCE TO RELATED APPLICATIONS

This is a national phase application of International Application No. PCT/EP2020/064059, filed 20 May 2020, which claims the benefit of German Patent Application No. 10 2019 114 461.2, filed 29 May 2019, the disclosures of which are incorporated, in their entireties herein, by this reference.

TECHNICAL FIELD

The invention relates to a method for producing a prosthesis liner for use in a prosthesis socket which has a receiving space, with a distal end and a proximal edge, for a stump of a patient and the prosthesis liner, a system consisting of a prosthesis socket and of a prosthesis liner, and also a prosthesis liner as such.

BACKGROUND

Prostheses replace missing or lost limbs in terms of the function and/or the appearance of the latter. The prosthesis itself is placed on a stump and fastened thereto. There are different systems for the fastening: one fastening system provides what is known as vacuum socket technology, in which the volume between the stump and an inner wall of the prosthesis socket is evacuated when the latter is fitted in place. For sealing and padding, a prosthesis liner can be arranged on the stump, which prosthesis liner generally has a closed distal end and a proximal access opening and surrounds the stump. Between the outer wall of the liner and the inner wall of the prosthesis socket, the insertion of the stump fitted with the prosthesis liner forms a volume that is evacuated, resulting in a force-fit connection between the prosthesis socket and the prosthesis liner. The prosthesis liner adheres to the prosthesis stump by means of adhesive forces, such that the prosthesis socket and the components attached to the prosthesis socket are fastened on the patient's stump. In order to achieve permanent fastening of the prosthesis socket, it is necessary to seal off the volume from the atmosphere. For this purpose, so-called caps or cuffs are provided, which are pulled over the proximal edge of the prosthesis socket and bear on the outer face of the prosthesis liner or the stump, such that no air can enter the gap between the proximal edge of the prosthesis socket and the prosthesis liner or the stump. As an alternative to a cuff or also a cap, sealing lips can be arranged or fixed on the outer face of the liner or on the inner face of the prosthesis socket in order to seal off a volume.

The prosthesis socket is generally made from a dimensionally stable material in order to have sufficient stability and strength to arrange further prosthesis components thereon and to provide a support function for the soft-tissue components. The proximal edge of the prosthesis socket is raised as high as possible in order to be able to securely accommodate the limb stump. In the case of a lower leg socket, the proximal edge protrudes medially and laterally as far as the knee condyles and is cut deep in the tibial region and in the popliteal region. A forearm socket has a similar construction. In the case of a thigh socket, a lateral elevation is formed in order to provide lateral stability. Prosthesis sockets are generally custom-made products that are produced to match the shape of the stump. Prosthesis liners are often standard products made of elastic material that can be adapted to different stump shapes. To be able to fit a wide variety of stump lengths with prefabricated prosthesis liners, sealing lips are usually arranged quite far distally or displaceably on the liner such that the proximal portion of the liner can be shortened on an individual basis without adversely affecting the function of the sealing element. The respective seal between prosthesis liner and prosthesis socket is therefore in this case a compromise between industrial producibility and the largest possible volume to be sealed in the socket.

U.S. Pat. No. 10,376,392 B2 discloses a system composed of a prosthesis socket and of a seal inside the prosthesis socket and of an annular inner rim, wherein the rim is arranged in a recess in the prosthesis socket. The recess or groove can be designed to follow the contour of the upper edge of the prosthesis socket.

SUMMARY

WO 2018/015736 A1 relates to a seal for a prosthesis liner with a tubular carrier and with one or more sealing lips, which protrude radially from the carrier and extend all around the latter. At least one of the sealing lips extends in an undulating shape around the carrier in the axial direction. It likewise relates to a prosthesis liner which has at least one circumferential sealing lip extending in an undulating shape in the axial direction.

The problem addressed by the present invention is to make available a method for producing a prosthesis liner and a system composed of a prosthesis socket and prosthesis liner, with which it is possible to allow the prosthesis socket to be securely fastened to a stump.

According to the invention, this problem is solved by a method having the features of the main claim and by a system having the features of the additional independent claim. Advantageous embodiments and developments of the invention are disclosed in the subclaims, the description and the figures.

In the method for producing a prosthesis liner for use in a prosthesis socket which has a receiving space, with a distal end and a proximal edge, for a stump and the prosthesis liner placed on the stump, provision is made that a sealing lip profile on the outer face of the prosthesis liner is determined corresponding to the profile of a height contour of the proximal edge of the prosthesis socket or based on existing, known anatomical characteristics of the stump. A sealing lip on the outer face of the prosthesis liner is arranged along the determined sealing lip profile. Thus, in the fitted state, the sealing lip profile follows the height contour of the proximal edge of the prosthesis socket and is designed corresponding to the upper end geometry of the prosthesis socket. The position of the sealing lip on the prosthesis liner is determined such that the sealing lip is arranged distally with respect to the proximal edge of the prosthesis socket when the prosthesis liner placed on the prosthesis stump is inserted fully into the prosthesis socket. On account of the sealing lip profile corresponding to the proximal end geometry of the prosthesis socket, it is possible to arrange the sealing lip, in the fitted state of the prosthesis liner, as far as possible proximally in the prosthesis socket and thus to achieve a maximum sealed surface of the volume. Using the maximized surface distally with respect to the sealing lip, it is possible to apply a maximum force, with the greatest possible and uniform distribution of the force, in order to hold the prosthesis socket on the prosthesis liner. On account of the geometry individually adapted to the proximal edge of the prosthesis socket and on account of a corresponding profile of the sealing lip, the mechanical quality of the interface is maximized and the loads on the stump, in particular on the amputation stump, are reduced. This increases the comfort for the user and produces a secure connection between the prosthesis socket and the stump. The sealing lip profile can, for example, be determined on the basis of an existing or calculated (particularly in digital form) profile of the proximal edge of a prosthesis socket. The known profile of the proximal edge of the prosthesis socket serves as a reference for the sealing lip profile, which is determined correspondingly. The sealing lip profile can likewise be determined on the basis of a scanned stump or on the basis of data obtained in some other way and relating to the shape and/or nature of the stump or of its anatomical features. The digitally available or calculated anatomy can serve as a basis for the prosthesis liner that is to be manufactured and also for the prosthesis socket that is to be manufactured. The prosthesis liner, possibly also the prosthesis socket, is modeled digitally around the model or digital image of the stump. The shape corresponds substantially to the outer contour of the stump, with add-ons for padding on the liner and, if necessary, adjustments to the prosthesis socket for relief regions or compression regions to compensate for volume fluctuations. The prosthesis liner can also be designed only on the basis of the stump model or of the digital image of the stump and/or of the prosthesis socket and converted into a digital data set, wherein the sealing lip profile can be determined on the basis of the anatomical characteristics without an already existing or calculated prosthesis socket data set.

In a development of the invention, the height contour of the proximal edge of the prosthesis socket is detected before the sealing lip profile is determined. The height contour, i.e. the profile in the proximal-distal direction of the proximal edge of the prosthesis socket, forms the profile of the upper end geometry of the prosthesis socket. In addition to the detection of a height contour of an already physically existing prosthesis socket, for example by a scanning method, by driving a height sensor along the proximal edge or parallel thereto and assigning the height data to the circumference coordinates or by means of a contactless measurement, for example optical measuring methods or other types of scanning, the determination can also be made solely on the basis of data concerning a prosthesis socket, in particular a prosthesis socket that is yet to be manufactured. If a 3D model or a data set already exists on the basis of which the prosthesis socket is intended to be manufactured, the sealing lip profile can be determined on the basis of these data and the prosthesis liner manufactured.

In a development of the invention, provision is made that the prosthesis liner is manufactured additively, for example in the context of a rapid liquid printing process, in order to be able to effect a quick and one-piece and individual adaptation of the prosthesis liner to the respective height contour and, if necessary, circumferential contour of the prosthesis socket. The rapid liquid printing process is described, for example, in US 2018-281295 A1. Alternatively, the sealing lip can be permanently fixed along the determined sealing lip profile on the outer face of the prosthesis liner, for example glued, welded, cast on or crosslinked or fixed on the outer face of the liner in an additive manufacturing process. In the region of the contact face between the sealing lip and a base body of the prosthesis liner, there is a cohesively bonded and in particular air-impermeable connection. The sealing lip can be formed separately and then applied and fixed along the determined sealing lip profile; alternatively, the sealing lip can be cast on and thus integrally molded, or the additive manufacturing of the sealing lip can preferably take place along the sealing lip profile on a base body that is not yet fully crosslinked. The sealing lip profile can be drawn on the prosthesis liner or indicated by an elevation or a depression along the sealing lip profile, in order to make available a positioning aid for a separate sealing lip that is to be fixed or integrally molded or additively determined.

The sealing lip can be arranged on the prosthesis liner in a manner offset in the distal direction with respect to the proximal edge of the prosthesis socket, in order to prevent the sealing lip from protruding proximally beyond the proximal edge of the prosthesis socket when the prosthesis liner is in the fitted and fully inserted state. By the shift or displacement in the distal direction away from the proximal edge of the prosthesis socket, a safety zone is established through which, for example, deviations in the intended orientation of the prosthesis liner on the stump can be compensated.

The profile of the height contour takes place in the proximal-distal direction and takes into account the total length of the prosthesis socket and thus also the distance of the sealing lip profile from the distal end of the prosthesis liner. Alternatively or in addition, the circumferential contour can also be detected over the circumference, in order to be able to adapt different heights of the sealing lip, i.e. the radial distance from the outer edge of the sealing lip to the base body of the prosthesis liner, to the respective patient.

The sealing lip can be arranged over the circumference of the prosthesis liner at the same distance in the proximal-distal direction from the proximal edge of the prosthesis socket, that is to say can extend substantially identical to the height contour of the proximal edge of the prosthesis socket.

The sealing lip can be arranged in a sealing lip region that is wider than the sealing lip itself and represents an assembly region within which a separate sealing lip can be arranged and fixed. The sealing lip region serves to facilitate production and also makes it possible, in an additive manufacturing process, to arrange, cast on, mold or form the sealing lip itself within a predetermined region in the proximal-distal direction. The proximal and distal border of the sealing lip region corresponds to the height contour of the proximal edge of the prosthesis socket.

The sealing lip region can, for example, be twice as wide as the sealing lip at the transition thereof to a prosthesis liner base body.

The height contour or the height contour and the circumferential contour of the prosthesis socket can be detected optically. The detected image data form a basis for a digital 3D model, for which or from which a data set is created. Based on the data set of the 3D model, the sealing lip profile or the sealing lip profile and the sealing lip shape are determined as a function of the detected height contour or the detected circumferential contour and height contour. The height contour can also be detected from data already available, for example a 3D model of the socket, without a prosthesis socket having to be physically present. If, for example, a prosthesis socket is created in an additive or another manufacturing process on the basis of a data set for a limb stump, for example an amputation stump, the inner contour of the prosthesis socket substantially follows the outer contour of the stump with an allowance for volume fluctuations and, if necessary, the material thickness of the prosthesis liner. If the prosthesis socket is not produced on the basis of digital data, for example taken from the stump itself or from a plaster model, the inner contour of an already existing prosthesis socket can be detected optically or in some other way and stored in a computer system. Based on the comparison of the outer contour of the stump and the inner contour of the prosthesis socket and the height contour of the edge of the prosthesis socket at the proximal end, which is also present in the 3D model, the position and the profile of the sealing lip on the outer face of the prosthesis liner are then determined. The height and shape and also the thickness of the prosthesis liner or prosthesis liner base body can likewise be determined and processed as a data set for manufacture in an additive manufacturing process. In the context of the additive manufacturing process, for example in the context of a rapid liquid printing process, the prosthesis liner can then be produced with the sealing lip profile and sealing lip height and/or sealing lip thickness adapted to the height contour and/or circumferential contour. The profile of the sealing lip can also be determined directly from anatomical data, for example on the basis of a scan of a stump. The height contour and the circumferential contour of the socket can then be determined from the sealing lip profile that is initially considered suitable or optimal, such that the sealing lip profile serves as a reference value for the profile of the proximal edge of the prosthesis socket. Or the height contour and the circumferential contour of the socket are likewise determined from the anatomical data of the scan. As a result, the profile of the sealing lip corresponds to the profile of the height contour of the prosthesis socket, regardless of whether the sealing lip profile is created and determined depending on the first determined height contour of the prosthesis socket, the height contour of the prosthesis socket is created or determined depending on the initially determined sealing lip profile, or the sealing lip profile and the height contour are created and determined independently of one another, on the basis of the anatomical conditions, for example on the basis of the digital 3D stump model.

The height of the sealing lip can be determined as a function of a detected distance between an inner circumference of the prosthesis socket and an outer circumference of the stump to be inserted.

In the system consisting of a prosthesis socket and of a prosthesis liner, provision is made that the prosthesis socket has a receiving space for a stump fitted with the prosthesis liner. The prosthesis socket has a distal end and a proximal edge. The proximal edge of the prosthesis socket has a height contour and a circumferential contour. At least one sealing lip is formed or fixed on the outer side of the prosthesis liner facing the prosthesis socket, the sealing lip profile of the at least one sealing lip in the fully inserted state of the prosthesis liner corresponds to the profile of the height contour of the prosthesis socket, the sealing lip forms a sealing lip profile in the form of a three-dimensional curve. The sealing lip does not have to end flush with the proximal edge of the prosthesis socket; rather, provision is made for the sealing lip to be arranged on the prosthesis liner, following the closure contour, distally from the proximal edge of the prosthesis socket.

The prosthesis socket is designed with a closed wall distal to the at least one sealing lip in the fully inserted state of the fitted prosthesis liner, in order to produce the greatest possible interface region, such that a corresponding negative pressure can be generated over the largest possible surface area.

The prosthesis socket is preferably designed to be dimensionally stable in order to provide sufficient stability for receiving the stump with the liner and for the arrangement of further prosthesis components, for example prosthetic joints. The at least one sealing lip is attached or formed on a base body of the prosthesis liner and can have an uneven height over the circumference of the prosthesis liner, i.e. can protrude radially outward at different distances from a base body so as to compensate for shape fluctuations or shape differences between the outer contour of the stump and the inner contour of the prosthesis socket.

In a further development of the invention, provision is made that the at least one sealing lip is attached or formed on a base body of the prosthesis liner and has a non-uniform width over the circumference of the prosthesis liner in order to compensate for differences in the radial distance between the outer face of the base body in the fitted state and the inner face of the prosthesis socket. This ensures that the sealing lip always lies against the inner wall of the prosthesis socket when the stump is inserted with the liner. The different thickness or the different radial expansion over the circumference of the prosthesis liner is determined, for example, in a comparison between the scanned inner face of the prosthesis socket and the scanned outer face or the 3D model of the stump.

Preferably, the sealing lip profile does not lie in one plane and is therefore not rectilinear; instead, it describes a three-dimensional curve with an irregular height contour, i.e. a non-uniform distance to the distal end of the prosthesis liner or the prosthesis socket over the circumference.

The prosthesis liner for a system described above provides at least one sealing lip which is formed or fastened on an outer face of the prosthesis liner and which forms a sealing lip profile in the form of a three-dimensional curve. The sealing lip profile of the at least one sealing lip is designed corresponding to the profile of a height contour of a proximal edge of a prosthesis socket into which the prosthesis liner placed on a stump is intended to be inserted.

An exemplary embodiment of the invention is explained in more detail below with reference to the accompanying figures, in which:

DETAILED DESCRIPTION

Figure 1:
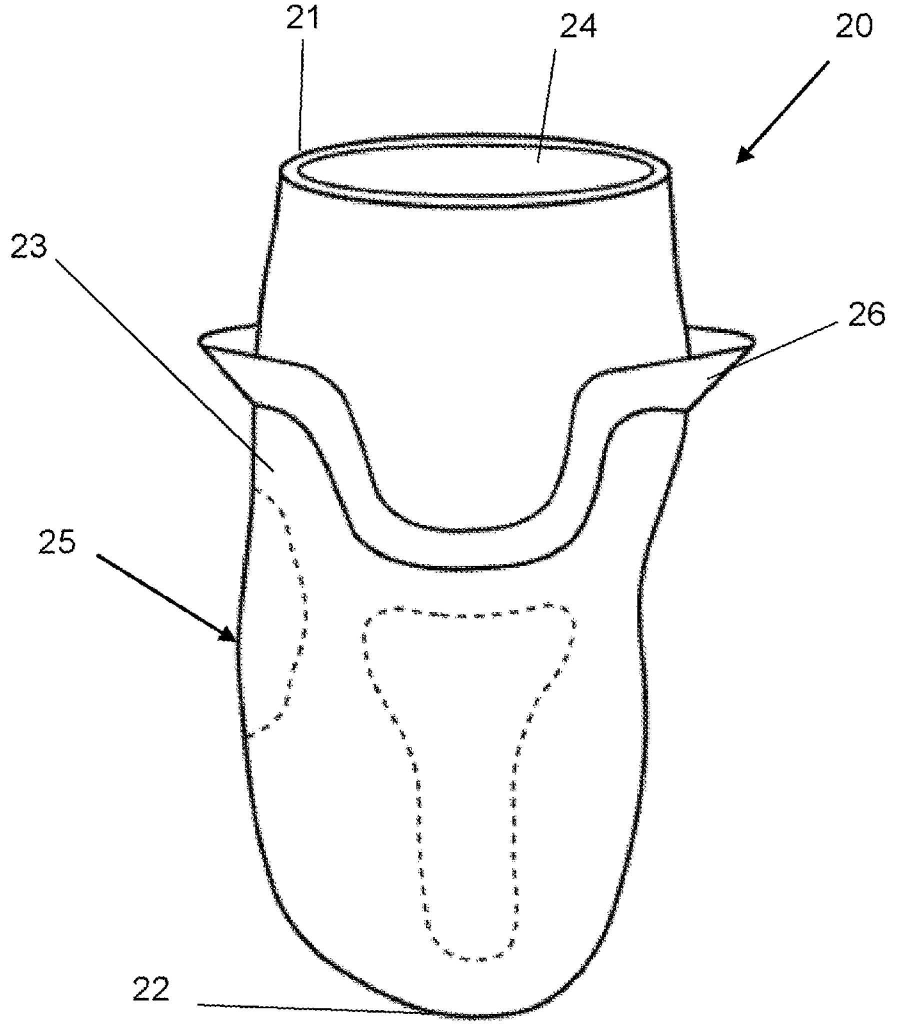
FIG. 1 shows a prosthesis liner on its own.

FIG. 1 shows a prosthesis liner 20 on its own, with a proximal edge 21 and a distal end region 22. The distal end region 22 is closed, and the proximal edge 21 circumferentially surrounds an access opening. The prosthesis liner 20 has a base body 25 with an outer face 23 and an inner face 24. The base body 25 is flexible and preferably elastic, at least in the circumferential direction. The inner face 24 of the base body 25 can be made of an adhesive polymer, for example silicone.

Alternatively, the inner face 24 can be completely or partially coated with an adhesive coating. The coating can be formed, for example, from a silicone or another polymer that adheres to the skin. The outer face 23 of the base body 25 can likewise be made of an elastomer or be at least partially coated with an elastomer. It is likewise possible that a textile is applied to the outer face 23 in order to equalize the pressure in a space between the prosthesis liner 20 and a prosthesis socket (not shown). Alternatively or in addition, elevations or channels can be arranged, for example formed or introduced or applied, on the outer face 23 in order to permit fluidic connections over the entire longitudinal extent, that is to say from distal to proximal, and all around the circumference.

Arranged on the base body 25 is a sealing lip 26 which forms a seal between the proximal region and the distal region of the prosthesis liner 20 in the inserted state in a prosthesis socket (not shown). The sealing lip 26 can be produced from an air-impermeable material or correspondingly coated, such that no air passes through the sealing lip 26. The sealing lip 26 can be made, for example, of a silicone or a polymer or be coated with such a material. One possible way of designing the sealing lip 26 is for it to be formed integrally with the base body 25, for example in the context of an additive manufacturing process, for example via the rapid liquid printing process, or by casting or during another primary forming process. The region located distally from the sealing lip 26 on the outer face 23 of the base body 25 can be provided with a structured surface, permitting a pressure distribution in regions spaced apart from one another. The structuring can be provided, for example, as a textile material, which can be glued on or laminated, or via channels and/or elevations on the outer face 23.

The sealing lip 26 protrudes radially from the base body 25 and is preferably elastic, such that the sealing lip 26 bears with its outer face, which faces away from the base body 25, on the prosthesis socket and presses against the latter. In the exemplary embodiment shown, the sealing lip 26 is not designed protruding perpendicularly from the outer face 23 of the base body 25, but is designed or arranged at an inclination. The inner face of the sealing lip 26, directed toward the base body 25, encloses between them an acute angle. In principle, it is also possible to provide a reverse orientation or to have the sealing lip 26 protruding perpendicularly. During the insertion of the prosthesis liner 20 into a prosthesis socket, the sealing lip is then generally folded back, such that an orientation is obtained in which the face of the sealing lip 26 oriented in the distal direction bears on the inner face of the prosthesis socket. If, in relation to the atmospheric pressure, there is a negative pressure in the volume sealed off by the sealing lip 26 between the prosthesis socket and the region located distally with respect to the sealing lip 26, the sealing lip 26 is pressed against the inner wall of the prosthesis socket, such that a self-intensifying sealing effect is established.

It will be seen from FIG. 1 that the proximal edge 21 of the prosthesis liner 20 is rectilinear or arranged in one plane, wherein the plane runs substantially perpendicular to the longitudinal extent of the prosthesis liner 20. By contrast, the sealing lip 26 does not run in a common plane, in particular not in a plane parallel or inclined with respect to the proximal edge 21 of the prosthesis liner 20, but instead along a three-dimensional curve that corresponds to the profile of the height contour of the prosthesis socket at the proximal edge thereof. The exemplary embodiment in FIG. 1 depicts a prosthesis liner 20 for a lower leg. The sealing lip 26 runs in the frontal region just below the patella and extends medially and laterally in the direction of the proximal edge 21. In the rear part of the prosthesis liner, the sealing lip 26 can extend down again in the distal direction. Such a profile corresponds to the profile of the proximal edge of a lower leg socket, which extends deeper in the frontal tibial region and in the popliteal region, that is to say is oriented there more in the distal direction than in the medial-lateral direction. Medially and laterally of the knee joint, prosthesis socket regions can be arranged extending further in the proximal direction, in order to achieve increased lateral stability and an improved contact between the lower leg socket and the stump.

Figure 2:
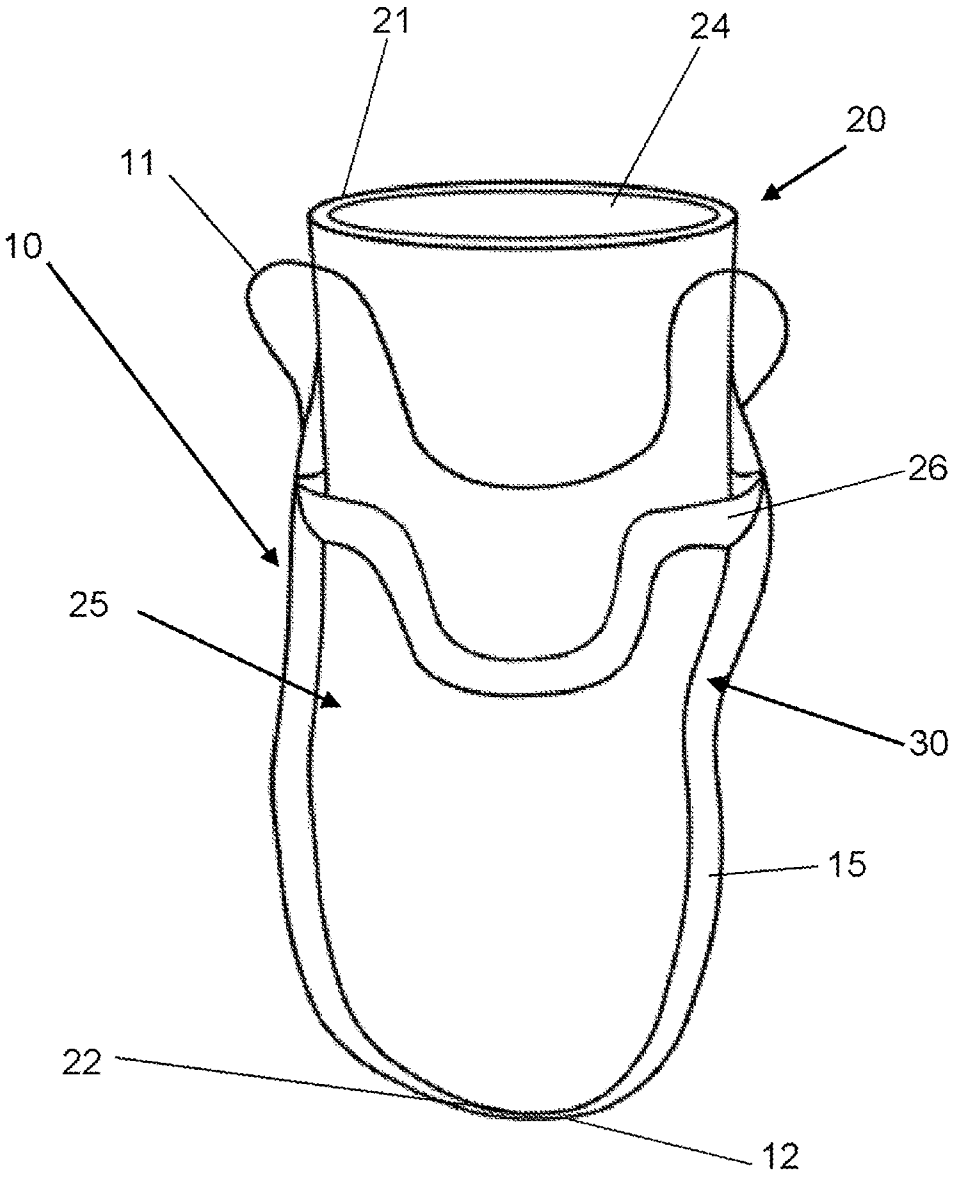
FIG. 2 shows a system composed of a prosthesis socket and of a prosthesis liner arranged thereon.

FIG. 2 shows a schematic view of the prosthesis liner 20 according to FIG. 1 in a fitted state. The prosthesis liner 20 is applied to the stump (not shown) and inserted into a prosthesis socket 10. The prosthesis socket 10 has a proximal edge 11, which does not lie in a flat plane but describes a three-dimensional curve. The prosthesis socket 10 has medially and laterally raised regions that extend further in the proximal direction than the regions that are arranged frontally and in the popliteal region. A cutout can be seen at the front that allows the kneecap to move. In the rear region of the hollow of the knee, a corresponding cutout or a corresponding depression is formed in order to allow the leg to bend without the dorsal region of the prosthesis socket being caught between the back of the thigh and the calf region.

The prosthesis liner 20 is fully inserted into a receiving space 15 of the prosthesis socket 10, that is to say the distal end 22 of the prosthesis liner 20 is located in the region of the distal end 12 of the prosthesis socket 10, optionally bearing thereon or spaced slightly apart therefrom, for example via padding. The sealing lip 26 bears on the inner wall of the prosthesis socket 10 and seals off a volume 30 between the inner wall of the prosthesis socket 10 and the outer wall 23 of the prosthesis liner 20 distally with respect to the sealing lip 26. The volume 30 is evacuated, for example by a pumping movement during walking, through an outlet valve or by a motor-driven pump, i.e. brought to a pressure level that is below the atmospheric pressure.

It will be seen from FIG. 2 that the sealing lip profile corresponds to or follows the profile of the proximal edge 11 of the prosthesis socket 10 and is located or arranged, only offset in the distal direction, on the outer face of the base body 25. The sealing lip 26 ideally extends as close as possible to the proximal edge 11 of the prosthesis socket 10. In particular, the height profile or the height contour, that is to say the profile of the sealing lip 26 around the circumference of the base body 25 in the proximal-distal direction, corresponds to the height profile of the proximal edge 11 of the prosthesis socket. Slight deviations may be possible; in particular, the sealing lip profile can be determined in a region that is substantially parallel to the profile of the height contour of the proximal edge 11 of the prosthesis socket 10, wherein the proximal and distal border of the region is designed corresponding to the height contour profile of the proximal edge 11.

The contour in the circumferential direction, i.e. the contour of the inner circumference of the prosthesis socket 10 in the region of contact with the sealing lip 26, can also be detected. The contour of the outer circumference of the sealing lip 26 can then be designed corresponding to the profile of the circumferential contour in the region of the contact of the outer sealing lip edge on the inner face of the prosthesis socket 10, provided with an add-on such that the sealing lip 26 can bear on the inner face of the prosthesis socket 10 with slight pre-tensioning due to the restoring forces in the event of a deformation after the prosthesis liner 20 has been inserted in the prosthesis socket 10.

As an alternative to an embodiment of the prosthesis socket 10 as a lower leg socket with elevations on the medial and lateral sides, it is possible, for example, that an embodiment as a thigh socket can have an elevation laterally on just one side, which reaches approximately as far as the axis of rotation of the hip joint. On the medial side of the thigh, a cutout that is offset in the distal direction is formed accordingly, resulting in a corresponding sealing lip profile in a thigh liner.

To produce such a liner 20, the height contour of the prosthesis socket 10, which is usually made on an individual basis, is detected first of all. For this purpose, the height of the prosthesis socket 10 is also detected, i.e. the distance from the proximal edge 11 to the distal end 12 on the inner face of the prosthesis socket 10 over the circumference of the stump. The shape and the dimensions can preferably be detected optically, for example by image recording and image evaluation; alternative detection data such as scanning with measurement value sensors can also be effected. If the prosthesis socket 10 for production was already digitally modeled, the height contour can be detected directly from the digital model and used as a reference for the sealing lip profile.

On the basis of the detected profile of the height contour of the proximal edge 11, it is then determined where the sealing lip 26 should bear on the inner face of the prosthesis socket and thus where the sealing lip is to be arranged on the outer face 23 of the base body 25 of the prosthesis liner 20. The detected data are used to create a 3D data model. Using the data model of the prosthesis socket 10, the liner 20 is constructed, for example with a standard base body 25 and an individual sealing lip profile of the sealing lip 26, which is adapted to the profile of the proximal edge 11 of the prosthesis socket 10. The shape of the prosthesis liner 20 with the adapted sealing lip profile is likewise calculated as a 3D data model. The 3D data model is used to generate manufacturing data, which are then used to produce the prosthesis liner 20 using an additive manufacturing process, with the sealing lip profile corresponding to the profile of the proximal edge 11 of the prosthesis socket.

Figure 3:
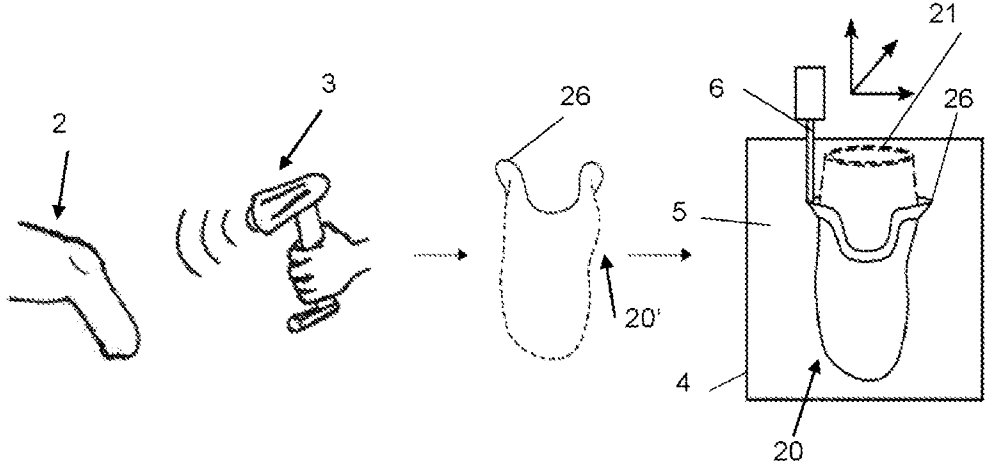
FIG. 3 shows a schematic representation of a variant of the production method.

FIG. 3 shows a possible sequence of a method for producing a prosthesis liner 20. From a stump 2, in this case a stump of the lower leg, an optical detection device 3 is used to record, i.e. scan, the outer contour of the stump 2. From the stump 2, a 3D model is created and processed in a computer (not shown). A data set 20', which substantially represents the shape of the subsequent prosthesis liner 20, is calculated on the basis of the 3D model. In addition to the sealing lip profile 26, the data set 20' also establishes the outer contour of the prosthesis liner 20, especially also the distal end 22 and, if appropriate, the material thickness of the prosthesis liner 20. By way of the data set 20', it is possible to define reinforcements, material weaknesses and the use of different materials, which are then used or incorporated during the manufacturing process. The actual prosthesis liner 20 can be manufactured on the basis of the data set 20'. In the exemplary embodiment, the proximal edge 21 or the profile of the proximal edge 21 of the actual prosthesis liner 20 is not yet fixed as in the data set 20'. The rest of the contour of the prosthesis liner 20 is indicated by the broken line. Based on the data set 20' or on the basic data from the scan, a data set for the prosthesis socket can be created which forms the basis for the manufacture of the latter, for example in an additive manufacturing process. The sealing lip profile 26 is defined in space as a contour line and can serve as a reference for the profile of the contour of the proximal edge of the prosthesis socket. The sealing lip profile of the sealing lip 26 on the outer face of a prosthesis liner 20 that is yet to be manufactured can therefore be determined first, and the prosthesis socket is designed thereafter. Conversely, there is the possibility of adapting the sealing lip profile to an already determined contour of the proximal edge of a virtual or already existing prosthesis socket.

Based on the data set 20', the prosthesis liner 20 is produced in an additive manufacturing process. In the exemplary embodiment shown, the production takes place according to what is called a rapid liquid printing process, in which a support material 5 is arranged in a tank or storage container 4. By way of a nozzle 6, which can be moved three-dimensionally in space, the material of the prosthesis liner 20 is introduced into the support material 5 and the prosthesis liner 20 is additively manufactured. The dashed line indicates the proximal end contour of the prosthesis liner 20, which is rectilinear in the exemplary embodiment shown. The proximal end contour or the proximal edge 21 of the prosthesis liner can also extend in a manner corresponding to the profile of the sealing lip 26 or corresponding to the proximal edge of the prosthesis socket.

The invention claimed is:

1. A method for producing a prosthesis liner for use in a prosthesis socket which has a receiving space for a stump and the prosthesis liner, the prosthesis socket having a distal end and a proximal edge, said method comprising:

- determining a sealing lip profile on an outer face of the prosthesis liner corresponding to a profile of a height contour or a height and circumferential contour of the proximal edge of the prosthesis socket; and
- arranging a single sealing lip on the outer face of the prosthesis liner along the determined sealing lip profile, wherein a proximal edge of the single sealing lip is spaced distally from the proximal edge of the prosthesis socket, and wherein the single sealing lip forms the sealing lip profile in the form of a three-dimensional curve, wherein the prosthesis liner comprises a base body comprising a flexible and elastic material configured to adapt to a shape of the stump, and wherein the single sealing lip, the prosthesis liner, and the prosthesis socket are configured to define a sealed volume comprising an entire volume between the single sealing lip, the prosthesis liner, and the prosthesis socket distal to the single sealing lip when the single sealing lip is inserted into the prosthesis socket, wherein the single sealing lip is arranged at an inclination relative to the base body of the prosthesis liner to form a seal between the base body and the prosthesis socket.

2. The method as claimed in claim 1, wherein the height contour of the proximal edge of the prosthesis socket is detected before the sealing lip profile is determined.

3. The method as claimed in claim 1, wherein the prosthesis liner is additively manufactured, or wherein the single sealing lip is fixed along the determined sealing lip profile.

4. The method as claimed in claim 3, wherein the prosthesis liner is produced in a rapid liquid printing process.

5. The method as claimed in claim 1, wherein the single sealing lip is arranged on the prosthesis liner in a manner offset in a distal direction with respect to the proximal edge of the prosthesis socket.

6. The method as claimed in claim 1, wherein the profile of the height contour is detected in a proximal-distal direction and/or the profile of a circumferential contour is detected over a circumference of the prosthesis socket.

7. The method as claimed in claim 1, wherein the single sealing lip over a circumference of the prosthesis liner is arranged at a same distance in a proximal-distal direction from the proximal edge of the prosthesis socket.

8. The method as claimed in claim 1, wherein the single sealing lip is arranged in a sealing lip region which is wider than the single sealing lip and of which a proximal and distal border corresponds to the height contour of the proximal edge of the prosthesis socket.

9. The method as claimed in claim 8, wherein the sealing lip region is twice as wide as the single sealing lip at its transition to the base body of the prosthesis liner.

10. The method as claimed in claim 1, wherein the height contour or the height and circumferential contour of the prosthesis socket is detected optically, a digital 3D model is created, and the sealing lip profile or the sealing lip profile and a sealing lip height is determined as a function of the detected height contour or of the detected circumferential and height contour.

11. The method as claimed in claim 10, wherein the sealing lip height is determined as a function of a detected distance between an inner circumference of the prosthesis socket and an outer circumference of a stump that is to be inserted.

12. A system comprising a prosthesis socket and a prosthesis liner, wherein the prosthesis socket has a receiving space for a stump fitted with the prosthesis liner, the prosthesis socket has a distal end and a proximal edge, the proximal edge of the prosthesis socket has a height contour and a circumferential contour, and at least one sealing lip is formed or determined on an outer face of the prosthesis liner directed toward the prosthesis socket, and wherein a sealing lip profile of the at least one sealing lip corresponds, in a fully inserted state of the prosthesis liner, to a profile of the height contour of the prosthesis socket, wherein a proximal edge of the at least one sealing lip is spaced distally from the proximal edge of the prosthesis socket, and wherein the at least one sealing lip forms the sealing lip profile in a shape of a three-dimensional curve, wherein the prosthesis liner comprises a base body comprising a flexible and elastic material configured to adapt to a shape of the stump, and wherein the at least one sealing lip, the prosthesis liner, and the prosthesis socket define a sealed volume comprising an entire volume between the at least one sealing lip, the prosthesis liner, and the prosthesis socket distal to the at least one sealing lip when the at least one sealing lip is inserted into the prosthesis socket, wherein the sealing lip is arranged at an inclination relative to the base body of the prosthesis liner to form a seal between the base body and the prosthesis socket.

13. The system as claimed in claim 12, wherein when the prosthesis liner is in the fully inserted state, the prosthesis socket is designed with a closed wall distally with respect to the at least one sealing lip.

14. The system as claimed in claim 12, wherein the prosthesis socket is dimensionally stable.

15. The system as claimed in claim 12, wherein the at least one sealing lip is fastened or formed on the base body and has a non-uniform width over a circumference of the prosthesis liner.

16. The system as claimed in claim 12, wherein the sealing lip profile does not lie in one plane.

17. The system as claimed in claim 12, wherein the sealing lip profile of the at least one sealing lip is designed to correspond to the profile of a height contour of a proximal edge of a prosthesis socket.

18. A method for producing a prosthesis liner for use in a prosthesis socket which has a receiving space for a stump and the prosthesis liner, the prosthesis socket having a distal end and a proximal edge, the method comprising:

optically detecting a height contour or a height and circumferential contour of the proximal edge of the prosthesis socket;

determining a sealing lip profile on an outer face of the prosthesis liner;

creating a 3D model of the prosthesis liner, wherein the sealing lip profile or the sealing lip profile and a sealing lip height is determined as a function of the height contour or of the circumferential and height contour; and arranging a sealing lip on the outer face of the prosthesis liner along the determined sealing lip profile in a manner offset in a distal direction with respect to the proximal edge of the prosthesis socket, wherein the sealing lip profile corresponds to the profile of the height contour of the proximal edge of the prosthesis socket, wherein a proximal edge of the sealing lip is spaced distally from the proximal edge of the prosthesis socket, and wherein the sealing lip forms the sealing lip profile in the form of a three-dimensional curve, wherein the prosthesis liner comprises a base body comprising a flexible and elastic material configured to adapt to a shape of the stump, and wherein the sealing lip, the prosthesis liner, and the prosthesis socket are configured to define a sealed volume comprising an entire volume between the sealing lip, the prosthesis liner, and the prosthesis socket distal to the sealing lip when the sealing lip is inserted into the prosthesis socket, wherein the sealing lip is arranged at an inclination relative to the base body of the prosthesis liner to form a seal between the base body and the prosthesis socket.

19. The method of claim 18, wherein the sealing lip comprises a single sealing lip.

* * * * *